United States Patent [19]

Tyman et al.

[11] 4,352,944

[45] Oct. 5, 1982

[54] TREATMENT OF CASHEW NUT SHELL LIQUID

[75] Inventors: John H. P. Tyman, London, England; Mahesh S. Patel, Scottsdale, Ariz.; Anthony P. Manzara, Stillwater, Minn.

[73] Assignee: Minnesota Mining and Manufacturing Company, St. Paul, Minn.

[21] Appl. No.: 223,418

[22] Filed: Jan. 8, 1981

[30] Foreign Application Priority Data

Jan. 8, 1980 [GB] United Kingdom .................. 8000551

[51] Int. Cl.³ ............................................. C07C 37/68
[52] U.S. Cl. ................................... 568/766; 568/750; 568/753; 568/756

[58] Field of Search ............... 568/766, 763, 767, 750, 568/753, 756

[56] References Cited

U.S. PATENT DOCUMENTS

2,098,824  11/1937  Harvey ................................ 568/780
2,223,549  12/1940  Harvey ................................ 568/780

*Primary Examiner*—Werren B. Lone
*Attorney, Agent, or Firm*—Cruzan Alexander; Donald M. Sell; Mark A. Litman

[57] ABSTRACT

The components of cashew nut shell liquid have such similar physical characteristics that their separation into relatively pure components has been difficult and has prevented use of the oil in many technological areas. The reaction of certain components with bases prior to distillation enables increased separation efficiency.

9 Claims, No Drawings

4,352,944

TREATMENT OF CASHEW NUT SHELL LIQUID

FIELD OF THE INVENTION

This invention relates to the treatment of cashew nut shell liquid (CNSL) to reduce the content of dihydric phenols therein whereby the treated CNSL may be used in polymerization reactions to produce colorless or lightly colored products.

BACKGROUND OF THE INVENTION

Cashew nut shell liquid (CNSL) is extracted from the outer shell of the cashew nut obtained from the cashew nut tree, Anacardium Occidentale. In the shell CNSL comprises mainly anacardic acid (2-carboxy-3-pentadecadientyl phenyl) and related acids of different degrees of unsaturation, together with cardol (m-pentadecadienyl resorcinol). The liquid is extracted from the shells by a heating process which results in decarboxylation of the acids so that the material obtained consists of cardanol (I) and cardol (II) and related compounds of varying degrees of unsaturation. A typical analysis of technical CNSL is shown below:

[Structures: (I) cardanol $C_{15}H_{(31-n)}$ phenol with OH; (II) cardol $C_{15}H_{(31-n)}$ resorcinol; 2-methyl cardol with $H_3C$ group; anacardic acid with COOH and OH]

(I) 63%   (II) 11%   2-methyl cardol 2%

Polymer 23% anacardic acid 1%

The side chains exist in saturated (N=0), monoene (n=2), diene (n=4) and triene (n=6) forms with cis configuration.

The components of CNSL contain a phenolic hydroxyl group and an unsaturated side-chain giving the material a dual functionality in polymerization reactions. As well as reacting with aldehydes to give products analogous to conventional phenol formaldehyde resins, CNSL can also be polymerized via the unsaturated side-chain. This versatility has led to the use of CNSL in various industries. Historically the main outlet for CNSL has been in the manufacture of brake linings and clutch facings where it is compounded with asbestos. Other applications have included cements and adhesives, laminated board manufacture and insulating varnishes.

The polymerization products of CNSL are generally dark brown in color and therefore the application of CNSL in the surface coating industry has been limited to those situations in which color is relatively unimportant.

It has been established that the dark colors formed during the polymerization of CNSL are attributable to the presence of polyhydric phenols, primarily cardol. Therefore in order to obtain colorless or lightly colored resins suitable for use in surface coatings, it is necessary to use CNSL which is substantially free of polyhydric phenols, namely cardol.

Various methods of purifying CNSL are known. Technical CNSL can be distilled under high vacuum with wide bore distillation equipment or by molecular distillation to yield a cardanol/cardol mixture possessing a pale yellow color as distillate and a brown material as the residue. Upon standing, some reversion of color of the distillate does occur. The recovery of phenolic material is generally approximately 70%. A slight loss of cardanol occurs in the distillation but generally all fractions contain both cardanol and cardol and separation of the two is not obtained.

Pure cardanol, free of cardol, has been obtained by column chromatography, but this method is expensive and time consuming and it is not suitable for use on an industrial scale.

It is an aspect of the present invention to describe a method of treating CNSL to reduce the content of dihydric phenols therein.

SUMMARY OF THE INVENTION

Therefore according to the present invention there is provided a method of treating CNSL to reduce the content of dihydric phenols therein comprising contacting the CNSL with a compound which will react with the dihydric phenol content therein to produce a reaction product which is stable under distillation conditions and which will not form a reaction product with the monohydric phenol content, such as an amine which has a basicity above that of diethanolamine and which is not highly volatile under the subsequent distillation conditions or with a strong organic base hydroxide or with a hydroxide of a metal of Group IA or Group IIA of the Periodic Table for a period sufficient to allow the amine or hydroxide to react with the dihydric phenols present in the CNSL and thereafter distilling the resulting mixture under high vacuum (i.e., less than 2 mm Hg) at a temperature in the range 160° to 220° C. and collecting the distillate which comprises CNSL having a reduced content of dihydric phenols.

DETAILED DESCRIPTION OF THE INVENTION

We have found that contacting CNSL at ambient temperature with amines having a relatively high basicity has the effect of complexing the dihydric phenols so that, on distillation, the distillate has an increased cardanol and decreased cardol content compared with the starting CNSL. The time for which the amine and CNSL are contacted prior to distillation does not appear to significantly affect the distillate content provided there has been sufficient time for the amine and dihydric phenols to react. Thus there is little difference between the effect of a contact time of 24 hours and 7 days.

The method of treatment is effective on all grades of CNSL, for example, treatments of technical CNSL and once-distilled CNSL give similar results, i.e., both show an increased concentration of cardanol compared to the starting material. Also the distribution of unsaturated components in the CNSL is not altered significantly as the amine treatment is quite mild. Thus, the invention may be used to obtain a composition comprising at least 90% by weight of cardanol in which the ratio of triene to monoene constituents is at least 1:1.

The interaction between dihydric phenols and amines is undoubtedly complex and leads to colored products removable at the distillation stage but the first step is probably a 1:1 interaction of an acidic center with a strongly basic center. In the competition between cardol and cardanol, the former with its high first dissociation stage would be expected to combine with the amine in the following way:

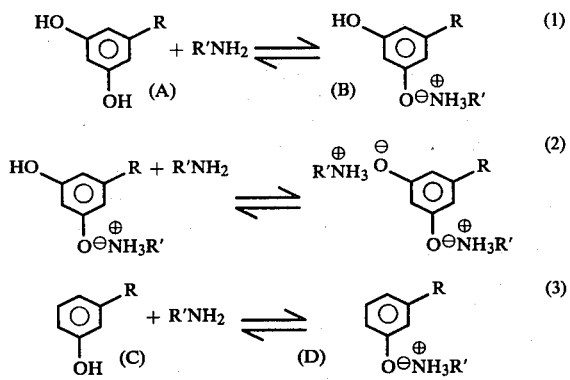

At ambient temperature the equilibrium of (1) probably is well to the right and (2) may be a relatively minor reaction. The equilibrium of (3) would be expected to favor more of the free phenol and to lie perhaps equally balanced between the phenol and the salt. Under distillation conditions the effect of (1) is to reduce the partial pressure $P_A$ of cardol to a low level whereas that of cardanol $P_C$ is probably the major contribution to the total pressure, after the free amine has been completely removed.

In the absence of the amine the partial pressure of the cardol is simply a product of its vapor pressure at that temperature and its molar fraction. Similarly that of cardanol is related to its vapor pressure and its corresponding mole fraction. Under these circumstances it is evident that $P_A$ is much higher than when the amine is present.

The amine must be present in an amount sufficient to react with all of the dihydric phenols present. Good results are obtained employing the amine in a 1:1 molar ration of amine:CNSL, the average molecular weight of CNSL being about 306.

Suitable amines for use in the invention include piperidine, N-(2-aminoethyl)ethanolamine, triethylamine and diethylenetriamine. Diethanolamine is not effective which is believed to be due to its low level of basicity. Preferably the amines used have a $K_b$ value of greater than $7.6 \times 10^{-6}$. There is considerable variation in the $K_b$ values for compounds reported in the literature and accordingly the precise figures provided for $K_b$ values are not necessarily accurate. Thus, whilst it is not possible to define a precise $K_b$ value for the suitable amines of the invention, the amines must have a relatively high basicity which is greater than that of diethanolamine.

In addition to their relatively high basicity the amines must form a reaction product with dihydric phenols which is stable under the distillation conditions so that the reaction product will remain in the residue. It has been found that certain amines having a relatively high basicity, e.g., n-butylamine which has a $K_b$ value of $3.9 \times 10^{-4}$, are not suitable for use in the invention. n-Butylamine is highly volatile and under the distillation conditions will volatilize disturbing the equilibrium of the reactions. It appears under the distillation conditions, the reaction product with the dihydric phenol dissociates to yield a dihydric phenol and accordingly the desired separation is not achieved. Similarly, ammonium hydroxide which is also highly volatile is not suitable for use in the invention.

Suitable hydroxides for use in the invention are those of metals of Groups IA and IIA of the Periodic Table, e.g. sodium, potassium, calcium and magnesium, hydroxides. Strong organic base hydroxides such as benzyl trimethylammonium hydroxide are also useful.

The distillation conditions are generally similar to those used for the conventional distillation of CNSL and the important parameters are discussed for example in A. K. Misra and G. N. Pandey, Chem. Age. India, 1976, 27, 944. The distillation should be conducted under high vacuum and at a temperature in the range 180° to 210° C., preferably below 200° C. The distillation may be conducted under a nitrogen atmosphere or in the presence of an antioxidant, e.g. 6-tert-butyl-3-pentadecylphenol. The preferred apparatus includes a Vigreux column in which case the cardol content of CNSL may be substantially completely removed. However, even a short still head section will significantly reduce the cardol content, e.g. from 20 to 6%.

The distillation is preferably conducted as rapidly as conditions will allow since thermal polymerization products form upon prolonged exposure to high temperatures. The first fraction which is collected comprises free amine and is discarded. The remaining fractions comprising cardanol are collected and any trace of amine in the distillate may be removed by conventional means, e.g., by washing with water.

The distillate obtained from the process of the invention may be used to prepare colorless or lightly colored polymeric products and is suitable for use in surface coating formulations. The residue which is believed to contain a cardol/amine salt may be separated from the amine by acid treatment and solvent extraction. This residue may be used to make polymerization products which will be colored as in the case of conventional CNSL polymerization products and may be used in similar applications. Thus, both the residue and distillate from the process of the invention are useful industrially.

The invention will now be further illustrated by the following Examples.

EXAMPLE 1

Technical CNSL of Brazilian origin and distilled CNSL obtained from it were used in the present work. Material of this origin tends to be richer in cardol. The average molecular weight was taken to be 306 based upon cardanol (average dienoid, m.w. 300) and cardol (m.w. 314, average trienoid). Three amines were used, namely diethylenetriamine (V), N-(2-aminoethyl)ethanolamine (VI) and diethanolamine (VII), which are structurally related.

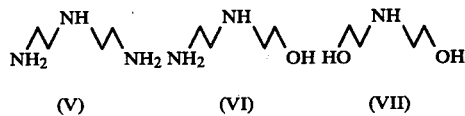

Different molar proportions of the triamine (DETA) (V) were used with distilled CNSL (1.0 mole), from 0.25, 0.50 to 1.0. In the case of Technical CNSL (having more cardol initially present) the molar proportions of DETA were 1.0, 1.6 and 2.0 per mole of the CNSL. The mixtures in all cases were kept for 7 days and then distilled under high vacuum. After recovery of the amine, one fraction of cardanol which was considerably purified was collected. It had a boiling point of from 185° to 200°/0.1 mm. The distillation residue was still quite mobile and from this, cardol and the polymer from the original CNSL could be recovered.

In a typical experiment, technical CNSL (9.18 g) and DETA (3.09 g: 1 mole) were interacted at ambient temperature and the mixture after 7 days distilled through a short Vigreux type Claisen flask. DETA (74%) was recovered and then cardanol which, by thin layer chromatography (hereinafter TLC), possessed no cardanol.

In the distillations reported in the following Tables 1 and 2 a Vigreux column was not used but merely a short still head section. All products were examined by gas-liquid chromatography (hereinafter GLC) on a gas chromatographic apparatus equipped with an integrator upon a 3% SE30 type column after trimethylsilylation with bis-(trimethylsilyl)acetamide in a pyridine solution. In the calculation of the results, response fractions have not been used. The peak areas as printed out by integration have been normalized (expressed in % form).

The results from the experiments with Technical CNSL and amines are shown in Table 1 and from distilled CNSL and amines in Table 2. The control experiment shows that in the absence of amine the % cardol is halved as a result of distillation, but with DETA the cardol is further reduced directly from ca 20% to ca 6%. A 1 molar proportion suffices to achieve this. It is clear that the incorporation of a few theoretical plates, as with a Vigreux type column used in the earlier experiment, reduces the cardol to almost zero.

EXAMPLE 2

A series of runs was performed using different amines. 0.2 mole of the amines indicated in the table was mixed with 300 g of distilled CNSL (cardanol:cardol 90:10, 1.0 mole). When the mixture was stirred a mild exothermic reaction was noted. The mixture was allowed to stand for seven days at room temperature then distilled at 0.5 mm Hg. The major fraction (boiling at 180° to 185° C.) was analyzed by gas chromatography for cardanol and cardol. The results were as follows:

| Amine | % composition of distillate | |
|---|---|---|
| | Cardanol | Cardol |
| Diethylenetriamine | 98.9 | 0.0 |
| Piperidine | 96.1 | 2.2 |
| n-butylamine | 94.5 | 5.5 |

With the two lower-boiling amines, the dry-ice trap contained amine in amounts approaching complete recovery.

EXAMPLE 3

Effect of length of time of DETA treatment

Technical CNSL was treated with DETA (1 mole proportion) and the mixture distilled as in Example 1 after it had been allowed to stand for 24 hours instead of 7 days. The analytical results shown alongside those for the 7 day treatment indicate that a 24 hour treatment is quite effective. Probably an overnight procedure might well suffice.

TABLE 1

Distillation of Technical CNSL treated with Amines
% composition of Technical CNSL - Cardanol 77.1)
Cardol 18.8)
2-me-Cardol 4.1)
(9.18 g of Technical CNSL was used)

| Amine | % of CNSL recovered | % amine recovered | % composition of distillate | | | % Residue | % composition of residue | | |
|---|---|---|---|---|---|---|---|---|---|
| | | | Cardanol | Cardol | 2-me-Cardol | | Cardanol | Cardol | 2-me-Cardol |
| Blank(no amine) | 51.4 | — | 86.4 | 9.66 | 3.9 | 45.5 | 59.8 | 32.3 | 7.9 |
| Diethylenetri-amine(DETA)(1M) | 18.5 | — | 93.0 | 5.1 | 1.9 | 75.2 | 85.6 | 11.2 | 3.2 |
| DETA(1.6 M) | 48.8 | 87 | 91.1 | 6.8 | 2.1 | 46.8 | 75.1 | 21.7 | 4.24 |
| DETA(2 M) | 62.2 | 93 | 93.1 | 5.8 | 1.1 | 42.4 | 63.2 | 29.1 | 7.6 |
| Diethanolamine (1.5 M) | 56.4 | 80 | 88.0 | 9.7 | 2.3 | 42.5 | 55.7 | 33.9 | 10.4 |
| N-(2-Aminoethyl)-ethanol amine (1.5 M) | 18.3 | 83 | 92.4 | 5.3 | 2.3 | 70.1 | 75.5 | 19.8 | 4.7 |

TABLE 2

Distillation of distilled CNSL treated with Amines
Composition of distilled untreated CNSL - Cardanol 86.9)
Cardol 10.3)
2-me-Cardol 2.8)
(9.18 g distilled CNSL was used with different molar ratio of amine)

| Amine | % of CNSL recovered | % composition of distillate | | |
|---|---|---|---|---|
| | | Cardanol | Cardol | 2-me-Cardol |
| Diethylenetri-amine(DETA) (0.25 M) | 53.3 | 95.4 | 3.9 | 0.7 |
| DETA(0.50 M) | 62.3 | 97.7 | 2.0 | 0.4 |
| DETA(1.0 M) | 26.1 | 93.8 | 4.2 | 2.0 |

| Treatment | Technical CNSL % Composition of distillate | | |
|---|---|---|---|
| | Cardonal | Cardol | 2-Methyl-Cardol |
| 24 h with DETA(1 M) | 91.7 | 6.6 | 1.6 |
| 7 days with DETA(1 M) | 92.0 | 6.2 | 1.8 |

EXAMPLE 4

Effect of treatment with DETA and distillation upon the unsaturated composition

Fractions obtained in the distillation conducted as described in Example 1 were examined by GLC on 3% PEGA after silylation.

| Starting Material | % Composition of unsaturated constituents | | |
|---|---|---|---|
| | Triene | Diene | Monoene |
| Technical CNSL(control) | 47.68 | 19.70 | 32.62 |
| Cardanol(1 M, DETA)24 h | 43.2 | 23.0 | 33.8 |
| Cardanol(1 M, DETA)7 days | 45.7 | 20.4 | 33.9 |
| Distilled CNSL(control) | 31.8 | 19.9 | 47.3 |
| Cardanol(1 M, DETA)7 days | 31.7 | 21.6 | 46.7 |

It is clear that the mild conditions of DETA treatment and the subsequent distillation in no way alter the unsaturated composition significantly.

EXAMPLE 5

Recovery of phenols from the residues obtained from distilled CNSL

Several combined residues from similar DETA treatments and distillations were distilled again to recover the phenols. The results of GLC analysis are shown below.

| Component | % Composition | | |
|---|---|---|---|
| | Before Distillation | After Distillation | |
| | | 1st Fraction | 2nd Fraction |
| Cardanol | 77 | 89.5 | 77.2 |
| Cardol | 17.8 | 8.2 | 17.8 |
| 2-Methyl-Cardol | 7.2 | 2.3 | |

These results show that the residue is enriched in cardol and that further useful material may be recovered from bulked residues.

EXAMPLE 6

Recovery of cardol from the distillation residues

The phenolic residual material from DETA treatment is believed to contain cardol as the cardol/DETA 'salt'. The complete recovery of cardol may require acidic treatment of the residue. The GLC analyses of the residue with and without this treatment do not differ widely and indicate that the method (of silylation) is probably estimating all the cardol present. From the point of view of utilization of the residue in polymerization reactions with formaldehyde it may be necessary to remove the DETA. Acid treatment and solvent extraction worked quite satisfactorily.

| Component | % Composition | |
|---|---|---|
| | Untreated residue | Acid washed residue |
| Cardanol | 44.3 | 47.1 |
| Cardol | 45.1 | 42.5 |
| 2-methyl-cardol | 10.6 | 10.3 |

EXAMPLE 7

Effect of base strength upon the separation of cardanol from cardol

The $K_b$ values of a number of bases which have been tested in the process of the invention in a manner analogous to that of Examples 1 and 2 are shown below together with their usefulness in the cardol/cardanol separation.

| Base | $K_b$* | Effectiveness (in cardol removal) |
|---|---|---|
| piperidine | $1.7 \times 10^{-3}$ | excellent |
| N—(2-aminoethyl)-ethanolamine | $6.6 \times 10^{-5}$ | excellent |
| n-butylamine | $3.9 \times 10^{-4}$ | not effective |
| DETA | $4.5 \times 10^{-5}$ | excellent |
| triethylamine | $4.5 \times 10^{-4}$ | excellent |
| Diethanolamine | $7.6 \times 110^{-6}$ | not effective |

*values from $K_b = \frac{[BH][OH^\ominus]}{[B]}$

The extent to which $K_b$ values determined in aqueous solution have any relevance to the non-aqueous environment arising in phenolic treatments is debatable.

Diethanolamine, which has a low $K_b$ is ineffective. For the effective compounds, the $K_b$ values range between $5.0 \times 10^{-5}$ and $160 \times 10^{-5}$, a magnitude difference of between 10 and 20. Thus probably no generalization can be made except that a base with $K_b$ $160 \times 100^{-5}$ (or less) would probably be unlikely to be effective. The amines must not be highly volatile under the distillation conditions (i.e., between 160° and 220° C.) as evidence by n-butylamine which has a $K_b$ value within the required range and yet is ineffective.

EXAMPLE 8

Distillation of Technical CNSL with sodium hydroxide 9.18 g of Technical CNSL (cardanol 77.1%, cardol 18.8% and 2-methyl-cardol 4.1%) was treated with 2% w/w of NaOH for seven days at ambient temperatures and then distilled at between 180° and 200° C. The results were as follows:

| Component | Distillate % | Residue % |
|---|---|---|
| Cardanol | 93.71 | 71.02 |
| Cardol | 4.69 | 22.89 |
| 2-methyl-cardol | 1.60 | 6.09 |

We claim:
1. A method of treating cashew nut shell liquid to reduce the content of dihydric phenols therein comprising contacting the cashew nut shell liquid with a compound which will react with the dihydric phenol content therein to produce a reaction product which is stable under distillation conditions of high vacuum at 160° to 220° C. and which will not form a reaction product with the monohydric phenol content which is stable under the distillation conditions for a period sufficient to allow said compound to react with the dihydric phenols present in the cashew nut shell liquid and thereafter distilling the resulting mixture under high vacuum at a temperature in the range of 160° to 220° C. and collecting the distillate which comprises cashew nut shell liquid having at least 90% by weight of cardanol and a reduced content of dihydric phenols.

2. A method of treating cashew nut shell liquid to reduce the content of dihydric phenols therein comprising contacting the cashew nut shell liquid with a compound which will react with the dihydric phenol content therein to produce a reaction product which is stable under distillation conditions of high vacuum at 160° to 220° C. and which will not form a reaction product with the monohydric phenol content which is stable under the distillation conditions for a period sufficient to allow said compound to react with the dihydric phenols present in the cashew nut shell liquid and thereafter distilling the resulting mixture under high vacuum at a temperature in the range of 160° to 220° C. and collecting the distillate which comprises cashew nut shell liquid having at least 90% by weight of cardanol and a reduced content of dihydric phenols in which the compound with which the cashew nut shell liquid is contacted comprises (a) an amine no more volatile than n-butylamine and having a basicity higher than that of diethanolamine, (b) an organic base hydroxide, or (c) a hydroxide of a Group IA or Group IIA metal.

3. The method of claim 2 wherein an amine is used in a molar ratio of 1:1 with the components of the cashew nut shell liquid.

4. The method of claim 3 wherein said amine has a $K_b$ of at least $7.6 \times 10^{-6}$.

5. The method of claim 2 in which said compound is an amine selected from piperidine, N-(2-aminoethyl)ethanolamine, triethylamine, and diethylenetriamine.

6. The method of claims 2 or 3 performed under a nitrogen atmosphere or in the presence of an antioxidant.

7. The method of claim 2 wherein distillation is at a pressure of less than 2 mm Hg.

8. The method of claim 2 wherein said distillation is at a pressure of less than 2 mm Hg and said compound is selected from the group consisting of piperidine, N-(2-aminoethyl)ethanolamine, triethylamine, diethylenetriamine, sodium hydroxide, potassium hydroxide, calcium hydroxide, magnesium hydroxide and benzyltrimethylammonium hydroxide.

9. The method of claim 1 wherein distillation is at a pressure of less than 2 mm Hg.

* * * * *

UNITED STATES PATENT AND TRADEMARK OFFICE
CERTIFICATE OF CORRECTION

PATENT NO. : 4,352,944
DATED : October 5, 1982
INVENTOR(S) : Tyman et al.

It is certified that error appears in the above—identified patent and that said Letters Patent is hereby corrected as shown below:

Column 1, line 43, delete "(N=0)" and insert --(n=0)--.

Column 8, line 9, delete "7.6 X $110^{-6}$" and insert --7.6 X $10^{-6}$--.

Column 9, line 18 (claim 4), delete "7.6 X $10^{316}$ and insert --7.6 X $10^{-6}$--.

Signed and Sealed this

Twenty-fourth Day of May 1983

[SEAL]

Attest:

DONALD J. QUIGG

Attesting Officer     Acting Commissioner of Patents and Trademarks